(12) United States Patent
Pohl et al.

(10) Patent No.: US 8,343,522 B2
(45) Date of Patent: Jan. 1, 2013

(54) ANTIMICROBIAL FILMS, SPONGES AND SPONGE CLOTHS

(75) Inventors: Matthias Pohl, Oberursel (DE);
Klaus-Dieter Hammer, Mainz (DE);
Walter Lutz, Hochheim (DE)

(73) Assignee: Kalle GmbH, Wiesbaden (DE)

( * ) Notice: Subject to any disclaimer, the term of this patent is extended or adjusted under 35 U.S.C. 154(b) by 162 days.

(21) Appl. No.: 13/031,655

(22) Filed: Feb. 22, 2011

(65) Prior Publication Data

US 2011/0217347 A1 Sep. 8, 2011

(30) Foreign Application Priority Data

Mar. 2, 2010 (DE) .......................... 10 2010 009 852

(51) Int. Cl.
*A01N 25/00* (2006.01)
*A01N 25/34* (2006.01)

(52) U.S. Cl. ...................................................... 424/402

(58) Field of Classification Search .................... None
See application file for complete search history.

(56) References Cited

U.S. PATENT DOCUMENTS

| | | | |
|---|---|---|---|
| 2,979,419 A | 4/1961 | Hill et al. | |
| 8,129,419 B2 * | 3/2012 | Levy et al. | 514/373 |
| 2007/0020366 A1 | 1/2007 | Luchansky et al. | |
| 2009/0023790 A1 | 1/2009 | Levy et al. | |

FOREIGN PATENT DOCUMENTS

| | | |
|---|---|---|
| DE | 27 21 427 B1 | 11/1977 |
| DE | 32 40 847 A1 | 5/1984 |
| EP | 0 141 066 A1 | 5/1985 |
| EP | 0 263 434 A2 | 4/1988 |
| EP | 0 330 996 | 9/1989 |

* cited by examiner

*Primary Examiner* — Anand Desai
*Assistant Examiner* — Melissa Mercier
(74) *Attorney, Agent, or Firm* — ProPat, L.L.C.

(57) ABSTRACT

Antimicrobial film based on biopolymers, in particular cellulose and/or protein, or uncoated or coated textile material, and also an antimicrobial sponge or an antimicrobial sponge cloth based on regenerated or precipitated cellulose are provided. The film, the sponge or the sponge cloth is impregnated or coated with at least one α-amino acid ester, the α-amino group of which is acylated with a fatty acid, or the corresponding hydrochloride, and the α-amino acid ester is bound covalently, optionally also ionically, to the film, the sponge or the sponge cloth. The acylated α-amino acid ester is preferably N-lauroyl-L-arginine ethyl ester monohydrochloride (LAECl), N-lauroyl-L-arginine methyl ester monohydrochloride (LAMCl) or N-lauroyl-L-lysine ethyl ester hydrochloride (LLECl). The film is preferably in the form of a flexible tube and is provided as casing for foods, especially sausage products.

18 Claims, No Drawings

ANTIMICROBIAL FILMS, SPONGES AND SPONGE CLOTHS

CROSS-REFERENCE TO RELATED APPLICATIONS

This application claims priority to German Patent Application 10 2010 009 852.3 filed Mar. 2, 2010 which is hereby incorporated by reference herein in its entirety.

FIELD OF THE INVENTION

The invention relates to an antimicrobial film based on biopolymers or textile material and also to antimicrobial sponges or sponge cloths based on regenerated or precipitated cellulose. The films are preferably tubular and are provided for packaging foods, especially sausage products.

BACKGROUND OF THE INVENTION

Antimicrobial films and sponge cloths are already known. Likewise, antimicrobial tubular films are known which are used as food casings. This applies in particular to ready-to-fill premoistened cellulose fiber skins. These typically have a moisture fraction of from 20 to 40% by weight, based on their total weight. In addition, US 2007/0020366 A1 describes shrink-wrap plastic bags that are sprayed or impregnated with antimicrobial agents such as acid calciumsulfate (ACS) or lauramide arginine esters, especially ethyl lauroylarginate hydrochloride, in order to preserve, for example, ham.

Food casings based on polysaccharides or coated textile materials for sausage products having a moisture content greater than 20% that must be kept mold-free for soaking-free processing, may be made germ free:
a) by preparations containing fungicidal substances, such as sorbic acid, benzoic acid, propionic acid, esters of para-hydroxybenzoic acid or salts thereof (as described in U.S. Pat. No. 2,979,419),
b) by reducing the water activity ($a_w$) below 0.94 with glycerol and/or propanediol (as described in DE 2721427, whose United States equivalent is U.S. Pat. No. 4,867,204) or
c) by sterilization before packaging by irradiation with gamma rays, or treatment with oxidizing agents ($H_2O_2$, peroxides).

It is substantially more complicated to produce food casings for sausage products whose casings must remain reliably mold-free after processing, i.e. after soaking, stuffing and cooking or scalding even in the case of dry or semidry sausage or scalded-emulsion sausage or cooked-meat sausage.

For this purpose sorbic acid or poorly soluble fungicides such as glycerol monolaurate (EP 0 141 066, whose United States equivalent is U.S. Pat. No. 4,662,403) or isothiazolones (EP 0 330 996, whose United States equivalent is U.S. Pat. No. 4,940,615) bound in the manner of salt to polyamine-polyamide-epichlorohydrin resins (DE 32 40 847, whose United States equivalent is U.S. Pat. Nos. 3,617,312 and 2,979,419) or to casein/glyoxal coatings (EP 0 263 434) are known. The most effective preservation, however, was achieved with dimethyldidecylammonium chloride. The ammonium ions enter into an ionic bond with anionic groups such as, for example, with the carboxylate groups of the cellulose or the collagen (in the case of collagen-coated textile skins) or the amino groups of the polyamide or collagen. A slow-release action is achieved in this manner.

Cellulose sponges and cellulose sponge cloths which are softened, for example, with a moisture content of at least 70% may be kept mold-free when packaged up until use, for example by means of the abovementioned fungicidal substances or by sterilization with gamma rays or peroxides. It is substantially more difficult to maintain biocidal protection of cellulose sponges and cellulose sponge cloths after they have been repeatedly washed.

Alkyldimethylbenzylammonium chloride has proved to be an effective fungicide having slow-release action which can be removed only slowly by water, owing to the substantive attachment of the ammonium group to cotton fibers, which are used as internal reinforcement of the sponge cloths.

The preparations containing unbound readily soluble fungicides and bactericides, as mentioned under a), the methods according to b) and c), the application by simple spraying onto plastics surfaces, such as shrink-wrap bags, and also the preparations containing Resamin, casein sorbate, glycerol monolaurate or isothiazolones do not offer sufficient protection at high moistures, heavy contamination or relatively heavy germ pressure, especially in the case of dry or semidry sausages and scalded-emulsion sausages. At a relatively high spore pressure, e.g. during ripening of dry or semidry sausages, in addition to mold-ripened dry or semidry sausages or during the storage of twice-packaged scalded-emulsion sausages, they are completely unsuitable.

At a very high spore pressure and very long storage time under extreme conditions, a preparation containing dimethyldidecylammonium chloride is also not safe enough, in particular in the case of long soaking of the casings before stuffing and at a low application rate.

US 2009/0023790 A1 discloses antimicrobially active compositions which comprise a) N-methyl-1,2-benzoisothiazolin-3-one and b) at least one further microbiocide. The further microbiocide is ethyl lauroyl arginate hydrochloride (LAECl), cocamidopropyl-N-2-hydroxy-ethylcarbamoylm-ethyldimethylammonium chloride, Cu(II)-2-aminoethanolate and didecyldimethylammonium chloride, didecyldim-ethylammonium carbonate and bicarbonate, Cu(II)-aminoethanolate, glycerol monolaurate, propylene glycol monolaurate or propylene glycol caprylate. The compositions prevent the growth of microorganisms on a multiplicity of products including food packages made of plastic or paper, and wiping cloths. However, they can be extracted by washing and thus rapidly lose activity since they are not firmly bound to the support.

In the case of cellulose sponges and cellulose sponge cloths, for example, the preparations under a) and c) lead to mold and bacterial infection on repeated use. Also the action of the preparations containing alkyldimethylbenzylammonium chloride or isothiazolones decreases gradually with increasing extraction processes by washing.

SUMMARY OF ADVANTAGEOUS EMBODIMENTS OF THE INVENTION

It was therefore still the object to provide food casings based on biopolymers, in particular polysaccharides and/or proteins, or uncoated or coated textile material and also sponges and sponge cloths based on regenerated or precipitated cellulose, that are antimicrobial in the long term. The antimicrobial action should decrease as little as possible even after repeated contact with water. This is of importance particularly for sponges and sponge cloths based on cellulose hydrate.

Not only was a further increase in the fungicidal and bactericidal (antimicrobial) action necessary, but substances had to be found which are suitable for foods not only in the original form but also after hydrolytic cleavage. It had proved to be extraordinarily difficult to ensure reliable action against fungi and bacteria by agents that were completely harmless toxicologically.

This demanding object was achieved by an ester of an α-amino acid, such as lysine, arginine or phenylalanine, the α-amino group of which is acylated with a fatty acid, such as lauric acid or stearic acid.

DETAILED DESCRIPTION OF ADVANTAGEOUS EMBODIMENTS OF THE INVENTION

The subject matter of the present invention therefore relates to a film based on biopolymers or textile material and also to a sponge or a sponge cloth based on regenerated or precipitated cellulose, wherein the film, the sponge or the sponge cloth is impregnated or coated with an amino acid ester, the α-amino group of which is acylated with a fatty acid, or the corresponding hydrochloride, wherein the amino acid ester or the hydrochloride thereof is covalently bound to the film, the sponge or the sponge cloth. Preferably, the amino acid ester or hydrochloride thereof is also further ionically bound to the film, the sponge or the sponge cloth.

The expression "biopolymers", in the context of the present invention, is taken to mean, in particular, polysaccharides, proteins and also mixtures thereof. Polysaccharides are, in particular, cellulose, starch, alginic acid or alginate or derivatives thereof, for example starch acetate. Proteins are, in particular, collagen (fibers), gelatin and mixtures thereof.

In a preferred embodiment, the film is a tubular food casing. It can be based, in particular, on regenerated or precipitated cellulose and can optionally comprise a fiber reinforcement. The fiber reinforcement used is frequently a paper made of hemp fibers or abaca fibers. Such cellulose fiber skins have long been known and are commercially available. The tubular film is preferably impregnated or coated on the outside with the acylated amino acid ester (hydrochloride).

In another preferred embodiment, a casing based on uncoated or coated textile material is used. The expression "textile material" is taken to mean, in particular, woven fabric, loop-formingly knitted fabric, loop-drawingly knitted fabric or nonwovens. Depending on the intended use, the textile material can be coated, for example, with acrylic resins, polyvinylidene chloride (PVDC) or protein (in particular collagen and/or collagen fibers and/or gelatin). Acrylic resins and PVDC can be applied, for example, in the form of a dispersion. A plurality of layers of the same or different composition can also be applied to the textile material. Preferably, the textile material is only coated on one side. By means of the coating(s), the water vapor and/or oxygen permeability of the casing may be set correctly for use. The fibers for the textile material can be of cotton, viscose staple, silk, polyamide, polyester or mixtures thereof. Before the coating, the textile material expediently has a weight of 15 to 150 g/m$^2$, in particular from 20 to 100 g/m$^2$. Processes and devices for coating are generally known. The textile material is expediently coated as a flat good. In order to obtain a tubular casing, the textile material can be shaped to form a tube having overlapping longitudinal edges. The overlapping region is then fixed with a longitudinal seam. This can be, for example, a sewn or glued seam or a heat-sealed seam. After the coating and drying, but before the impregnation with the antimicrobially active substance, the weight of the textile material is generally 30 to 200 g/m$^2$, in particular 40 to 150 g/m$^2$.

The antimicrobially active substance, hereinafter also called N-acylamino acid ester, is used, preferably as quaternary ammonium compound, preferably as hydrochloride. It can be used as sole active ingredient, or in combination with other antimicrobial agents such as para-hydroxybenzoic acid (C1-C6)alkyl esters, salts thereof, benzoic acid, sorbic acid and salts thereof, propionic acid, etc.

The α-amino acid is preferably a L-α-amino acid, as occurs in nature in animal proteins. Preference is given to basic α-amino acids, such as lysine, histidine and arginine. However, hydrophobic α-amino acids can also be used, for example phenylalanine, tyrosine, valine, leucine or isoleucine. The ester of an amino acid is generally a—preferably straight-chain—$(C_1-C_6)$alkyl ester, in particular a methyl, ethyl, propyl, isopropyl, butyl, isobutyl, tert-butyl, pentyl, isopentyl, neopentyl, hexyl or isohexyl ester.

The fatty acid is generally a $C_{12}$ to $C_{20}$ fatty acid, preferably a fatty acid having 12, 14, 16, 18 or 20 carbon atoms. Saturated fatty acids are preferred. Particular preference is given to lauric acid, myristic acid, palmitic acid and stearic acid. The structural formula of a preferred N-acyl-α-amino acid ester hydrochloride is pictured hereinafter:

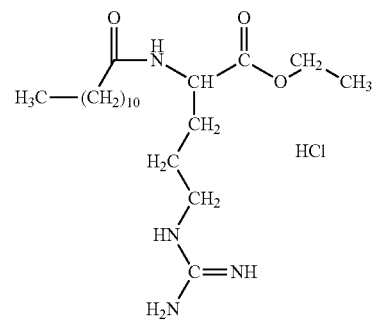

EXAMPLE

N$^α$-lauroyl-L-arginine ethyl ester monohydrochloride (LAECl) (CAS No. 60372-77-2)

Said α-amino acid derivatives and also processes for production thereof are known. Generally, the amino acid is esterified with an alkanol, for example ethanol, and then reacted with a fatty acid derivative, for example lauroyl chloride. LAECl has been used previously as a preservative in particular in foods, cosmetics and hair shampoo.

The quaternary ammonium groups due to the hydrochloride cause a firm electrostatic (salt-like) bond to the anionic functional groups such as, for example, to the carboxyl groups of the cellulose, the alginate or the collagen, or firmly bound preparation products on the surface.

The N-acyl amino acid ester hydrochloride can be used in the form of an up to 20% strength by weight solution in propylene glycol. It is soluble at 5% by weight in ethanol or glycerol and miscible with water. The active substance is covalently bound to the casing. For this purpose, aldehydes are used in particular, for which, in principle, formaldehyde, acetaldehyde, dialdehydes such as glyoxal, glutaraldehyde, or others, come into consideration. The fraction of the aldehydes is generally 3 to 5% by weight, based on the weight of the active substance.

The active substance is employed in the preparation solution in a concentration of 2 to 30% by weight, preferably 5 to 10% by weight, dissolved in polyethylene glycol (PEG), propanediol, glycerol and/or water. In addition, to the quaternary amino acid fatty acid ester, a further antimicrobial substance can be added, for example a para-hydroxybenzoic acid alkyl ester, a salt thereof, benzoic acid, sorbic acid or a sorbic acid salt, propionic acid etc. Preferably, the gel skin is treated with the preparation, for example in the case of cellulose casings, or the collagen-coated textile casing, before entry into the dryer, either by spraying or using a roller applicator. In the case of drying (under the action of heat), then a covalent bond to the casing surface takes place after addition of the aldehydes at an $NH_2$ group (imine or Schiff base) or at an OH group, via methylols.

For firm fixing of the active substance to casing surfaces made of, for example, cellulose, alginate or uncoated or coated textiles, in addition, a resin is useful, e.g. a polyamine-polyamide-epichlorohydrin resin, which is employed at a concentration of 1 to 5% by weight, preferably 2 to 3% by weight (solid). A covalent bond of the active compound is also achieved thereby. For treating unsoaked casings with the preparation, i.e. of prepared food casings having a moisture content above 20%, it is expedient to use the pure product, i.e. without wetting or embedding agents. By means of the bonding to the surface, in particular the covalent bond by means of aldehydes, for example glyoxal, the preparation becomes soaking- and scalding-resistant. In this manner a slow-release action is achieved, which is of great importance especially in the case of sponge cloths.

Mold and bacterial infection is a serious problem in the case of sausage products and other foods, which can lead to enormous losses; without treatment with a preparation, their lifetime is limited. With the cationic ester of an amino acid and a fatty acid such as $N^\alpha$-lauroyl-L-arginine ethyl ester monohydrochloride (LAECl) or $N^\alpha$-lauroyllysine ethyl ester monohydrochloride (LLECl), a completely surprising and unusual problem solution has now been found which is unusual not only for toxicological reasons, but also for the preparation offering particular conditions, because apart from a salt-type bond, a covalent bond is also possible. The result is a long-lasting slow-release action and suitability for a broad variety of applications, namely from soaking-free shirred sticks to scalded-emulsion sausage casings, for example for internally coated cellulose fiber skin types.

Application is possible without additional process steps, namely either by impregnation or spraying the gel skin before entering into the dryer or by spraying during rolling for moistening for soaking-free material. It is particularly important that scalded-emulsion sausages in the second packaging and dry or semidry sausages, apart from mold ripening, remain without infestation. With this novel covalently bonded biocidal treatment it has become possible to protect food casings based on polysaccharides such as cellulose, starch or alginate, or on textile materials, which are coated, for example, with collagen or thermoplastic polymers, and also sponge cloths based on cellulose hydrate against mold and bacterial infestation. The protection remains even after a plurality of washing operations, and so, in particular, the sponge cloths can be used over a relatively long time period.

Application of the biocidal treatment may be performed either by addition to the plasticizer solution, on spraying of non-soaked goods or by spraying before entry into the dryer for goods supplied dry. In the case of a flexible tubular food casing, the antimicrobial impregnation or coating is situated preferably on the outside.

The examples hereinafter serve for illustration of the invention. Percentages therein are taken to be percentages by weight unless stated otherwise, or is immediately clear from the context.

Example 1

An externally-viscosed cellulose hydrate flexible tube having a fiber paper insert of caliber 60 was, before entry into the dryer, passed through an impregnation trough which contained a 4% aqueous solution of LAECl and 3% glyoxal, based on the active substance.

Into the interior of the flexible tube was charged a customary adhesion impregnating solution (casein+glyoxal); the flexible tube was dried in the inflated state and moistened to 16 to 18%. During shirring of the casing, the moisture content was then increased to 25±2% by internal mandrel spraying; the non-soaked shirred sticks sealed into film did not show any mold or bacterial infestation after storage for any desired period under standard or tropical conditions.

In the ripening of dry or semidry sausage, likewise no mold formation was observed.

Example 2

A double-viscosed cellulose hydrate fiber flexible tube of caliber 60 having a viscose distribution 30/70 (exterior/interior) was, in the gel state before entry into the dryer, passed through an aqueous solution which contained 5% LAECl, 1% para-hydroxybenzoic acid methyl ester and 3% glyoxal, based on the active substance.

A customary adhesion impregnation for dry or semidry sausage was charged into the flexible tube interior; the flexible tube was then dried to 8 to 10% moisture in the inflated state. The shirred sticks were charged with dry or semidry sausage emulsion; during ripening they also remained mold-free even next to mold-ripened sausages.

Example 3

A double-viscosed cellulose hydrate flexible tube of caliber 60 having a viscose distribution 40/60 (exterior/interior), in the gel state before entry into the dryer, is passed through an aqueous solution which contained 6% LAECl and 3% glyoxal, based on the weight of the active substance.

A customary anchoring solution was charged into the flexible tube interior. The flexible tube was, as is customary, dried in the inflated state, wound up and internally coated with a PVDC dispersion in a second process step. Meat sausage emulsion was charged into sections of the sausage casing that were tied off at one end, and the sausages were then given a second packaging in film.

After a storage time of 6 weeks, still no mold infestation could be observed. On the cooked, inoculated long-life samples, after a 4-week incubation period, likewise no mold developed.

Example 4

An externally-viscosed cellulose hydrate flexible tube of caliber 60 is treated in the gel state, before drying, with a solution consisting of propanediol, water (mixing ratio 40:60), 3% $N^\alpha$-lauroylarginine ethyl ester hydrochloride (LAECl) and 3% by weight (solid) of a polyamine-polyamide-epichlorohydrin resin (or KYMENE® G3 x-cel from Hercules). The tube is dried, as is customary, in the inflated state and moistened to 16 to 18%.

The casings were then brought to a moisture of 25±2% by rolling for a non-soaked processability and finally processed. Despite subsequent packaging of the shirred sticks in film and storage under extreme conditions, even after a storage time of many months, neither mold nor bacterial infestation could be observed.

Example 5

A sponge cloth web, reinforced with cotton fibers, was passed from unrolling through a plasticizer bath that contained 18% $MgCl_2$ and 82% water.

This plasticizer bath was admixed with 0.5% $N^\alpha$-lauroylarginine ethyl ester monohydrochloride (LAECl) and 5% glutaraldehyde (based on the above substance). The completely impregnated sponge cloth web was freed of excess liquid using a squeeze-roll pair, in such a manner that the plasticized sponge cloth had a moisture content of 100 to 200%, based on its dry weight.

That which is claimed:

1. An antimicrobial film based on biopolymers or textile material or antimicrobial sponge or antimicrobial sponge cloth based on regenerated or precipitated cellulose comprising an impregnation or coating including at least one α-amino acid ester that has an α-amino group which is acylated with a fatty acid or the hydrochloride thereof,
wherein the α-amino acid ester is covalently bound to the film, the sponge or the sponge cloth.

2. The film, sponge or sponge cloth as claimed in claim 1, wherein the α-amino acid ester is additionally ionically bound to the film, the sponge or the sponge cloth.

3. The film as claimed in claim 1, wherein the film is tubular and the outside of said film is impregnated or coated with the acylated α-amino acid ester or the acylated α-amino acid ester hydrochloride.

4. The film as claimed in claim 3, wherein said film is based on regenerated or precipitated cellulose which comprises a reinforcement made of a fiber paper.

5. The film as claimed in claim 3, wherein said film is based on coated textile material.

6. The film as claimed in claim 1, wherein the biopolymers are polysaccharides, proteins or mixtures thereof.

7. The film as claimed in claim 6, wherein the biopolymers are cellulose, starch, alginic acid/alginate, collagen, collagen fibers, gelatin or mixtures thereof.

8. The sponge cloth as claimed in claim 1, wherein said sponge cloth comprises a reinforcement made of fibers or a plastic net.

9. The sponge cloth as claimed in claim 8, wherein the fibers have a length of 0.3 to 25 mm.

10. The sponge cloth as claimed in claim 8, wherein said fibers are cotton fibers.

11. The film, sponge or sponge cloth as claimed in claim 1, wherein the acylated α-amino acid ester hydrochloride is $N^\alpha$-lauroyl-L-arginine ethyl ester monohydrochloride, $N^\alpha$-lauroyl-L-arginine methyl ester monohydrochloride or $N^\alpha$-lauroyl-L-lysine ethyl ester monohydrochloride.

12. The film, sponge or sponge cloth as claimed in claim 1, wherein the acylated α-amino acid ester or the hydrochloride thereof is covalently bound to the film or sponge cloth via mono- or dialdehydes or polyamine-polyamide-epichlorohydrin resins.

13. The film, sponge or sponge cloth as claimed in claim 1, wherein the acylated α-amino acid ester or the hydrochloride thereof is combined with at least one further antibacterially active agent.

14. The film, sponge or sponge cloth as claimed in claim 13, wherein the further antibacterially active agent is para-hydroxybenzoic acid alkyl ester or a salt thereof, benzoic acid or a benzoate, sorbic acid or a sorbate.

15. A process for producing a film, a sponge or a sponge cloth as claimed in claim 1, said process comprising treating said film, sponge or sponge cloth with a solution of at least one N-acyl-α-amino acid ester hydrochloride, the solution comprising solvent and an agent that effects a covalent bond of the N-acyl-α-amino acid ester hydrochloride to the film, the sponge or the sponge cloth.

16. A process for producing a film, sponge or sponge cloth as claimed in claim 15, wherein the solvent is water and a monohydric or polyhydric alcohol.

17. A process for producing a film, sponge or sponge cloth as claimed in claim 16, wherein the alcohol is ethanol, propanediol, polyethylene glycol or glycerol.

18. A process for producing a film, sponge or sponge cloth as claimed in claim 15, wherein said treating comprises spraying on the solution, immersion into an impregnation bath containing the solution, or applying the solution via a roller applicator.

* * * * *